(12) United States Patent
Herold et al.

(10) Patent No.: US 8,003,640 B2
(45) Date of Patent: *Aug. 23, 2011

(54) ORGANIC COMPOUNDS

(75) Inventors: Peter Herold, Müchenstein (CH);
Stjepan Jelakovic, Freiburg (DE);
Robert Mah, Basel (CH); Vincenzo Tschinke, Binningen (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/745,100

(22) PCT Filed: Dec. 4, 2008

(86) PCT No.: PCT/EP2008/066747
§ 371 (c)(1),
(2), (4) Date: Aug. 16, 2010

(87) PCT Pub. No.: WO2009/071606
PCT Pub. Date: Jun. 11, 2009

(65) Prior Publication Data
US 2010/0303926 A1 Dec. 2, 2010

(30) Foreign Application Priority Data
Dec. 5, 2007 (EP) .................................... 07122363

(51) Int. Cl.
*C07D 413/12* (2006.01)
*A61K 31/538* (2006.01)
(52) U.S. Cl. .................................................. 514/230.5
(58) Field of Classification Search .................. 544/105; 514/230.5
See application file for complete search history.

(56) References Cited

U.S. PATENT DOCUMENTS

| 7,625,893 B2 * | 12/2009 | Herold et al. ............... 514/230.5 |
| 2007/0010511 A1 | 1/2007 | Herold et al. |
| 2008/0076766 A1 | 3/2008 | Herold et al. |
| 2009/0012055 A1 | 1/2009 | Herold et al. |
| 2009/0029981 A1 | 1/2009 | Herold et al. |

FOREIGN PATENT DOCUMENTS

| JP | 63-264573 | 11/1988 |
| WO | 97/09311 | 3/1997 |
| WO | 2005/037803 | 4/2005 |
| WO | 2005/061457 | 7/2005 |
| WO | 2006/005741 | 1/2006 |
| WO | 2006/103275 | 10/2006 |
| WO | 2007/082907 | 7/2007 |

OTHER PUBLICATIONS

Wolff, Manfred E. "Burger's Medicinal Chemistry and Drug Discovery, 5ed, vol. 1" John Wiley & Sons, 1995, pp. 975-977.*
Banker, G.S. et al, "Modern Pharmaceutices, 3ed." Marcel Dekker, New York, 1996, pp. 451 and 596.*
Märki et al., "Piperidine Renin Inhibitors: From Leads to Drug Candidates", Il Farmaco, vol. 56, 2001, pp. 21-27.
Güller et al., "Piperidine-Renin Inhibitors Compounds with Improved Physicochemical Properties", Bioorganic & Medicinal Chemistry Letters, vol. 9, 1999, pp. 1403-1408.
International Search Report issued Mar. 2, 2009 in International (PCT) Application No. PCT/EP2008/066747.

* cited by examiner

*Primary Examiner* — Kahsay T Habte
(74) *Attorney, Agent, or Firm* — Wenderoth, Lind & Ponack, L.L.P.

(57) ABSTRACT

The present invention relates to compounds of the general formula (I) and the salts thereof, preferably the pharmaceutically acceptable salts thereof; in which in which $R^1$ has the meaning explained in the description, a process for their preparation and the use of these compounds as medicines, especially as renin inhibitors.

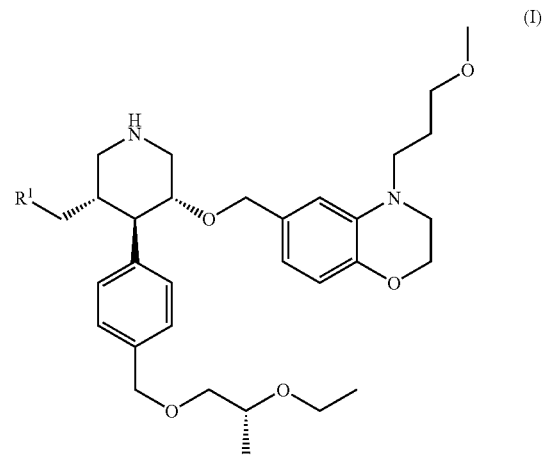

12 Claims, No Drawings

ORGANIC COMPOUNDS

This application is a U.S. national Phase filing of International Serial No. PCT/EP2008/066747 filed Dec. 4, 2008, and claims priority to EP application Serial No. 07122363.0 filed Dec. 5, 2007, the contents of which are incorporated herein by reference in their entirety.

FIELD OF THE INVENTION

The present invention relates to novel substituted 4-phenyl piperidines, to processes for their preparation and to the use of the compounds as medicines, in particular as renin inhibitors.

BACKGROUND OF THE INVENTION

Piperidine derivatives for use as medicines are known, for example from WO 97/09311. However, especially with regard to renin inhibition, there is still a need for highly potent active ingredients. In this context, the improvement of a compound's pharmacokinetic properties, resulting in better oral bioavailability, and/or it's overall safety profile are at the forefront. Properties directed towards better bioavailability are, for example, increased absorption, metabolic stability or solubility, or optimized lipophilicity. Properties directed towards a better safety profile are, for example, increased selectivity against drug metabolizing enzymes such as the cytochrome P450 enzymes.

DETAILED DESCRIPTION OF THE INVENTION

The invention therefore provides substituted 4-phenyl piperidines of the general formula

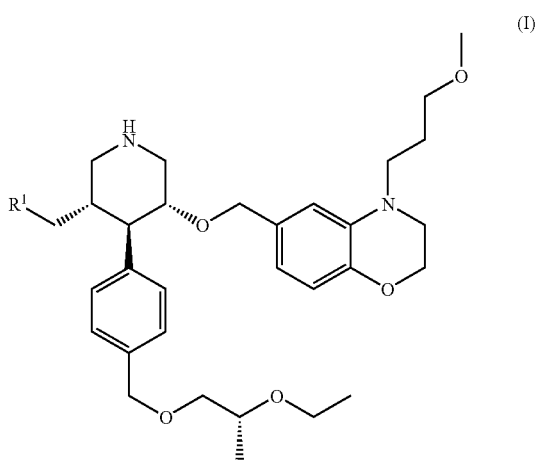

(I)

and their salts, preferably their pharmaceutically acceptable salts, in which $R^1$ is $C_{1-8}$-alkanoyloxy, $C_{1-8}$-alkanoyloxy-$C_{1-8}$-alkyl, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxy-carbonylamino, $C_{1-8}$-alkoxycarbonylamino-$C_{1-8}$-alkyl, $C_{0-8}$-alkylcarbonylamino, $C_{0-8}$-alkylcarbonylamino-$C_{1-8}$-alkyl, O—$C_{1-8}$-alkylated carboxyl, O—$C_{1-8}$-alkylated carboxyl-$C_{1-8}$-alkyl, optionally N-mono- or N,N-di-$C_{1-8}$-alkylated amino, optionally N-mono- or N,N-di-$C_{1-8}$-alkylated amino-$C_{1-8}$-alkyl, optionally N-mono- or N,N-di-$C_{1-8}$-alkylated amino-carbonylamino, optionally N-mono- or N,N-di-$C_{1-8}$-alkylated aminocarbonyl-amino-$C_{1-8}$-alkyl, heterocyclyl, heterocyclyl-$C_{1-8}$-alkyl, heterocyclyl-$C_{0-8}$-alkylcarbonyl-$C_{1-8}$-alkylamino, heterocyclyl-$C_{0-8}$-alkyl-carbonyl-$C_{0-8}$-alkylamino-$C_{1-8}$-alkyl, hetero-cyclyl-$C_{0-8}$-alkyl-carbonyl-$C_{1-8}$-alkyl, cycloalkyl-$C_{0-8}$-alkyl-carbonyl-$C_{0-8}$-alkylamino, cycloalkyl-$C_{0-8}$-alkyl-carbonyl-$C_{0-8}$-alkylamino-$C_{1-8}$-alkyl, hydroxyl, hydroxy substituted $C_{1-8}$-alkyl, optionally N-mono-, -di- or -tri-$C_{1-8}$-alkylated or heterocyclyl-substituted ureido or optionally N-mono-, -di- or -tri-$C_{1-8}$-alkylated or heterocyclyl-substituted ureido-$C_{1-8}$-alkyl and whereby the heterocyclyl and cycloalkyl radicals mentioned hereinbefore are unsubstituted or substituted.

The meaning of "$C_0$-alkyl" in the above (and hereinafter) mentioned $C_{0-8}$-alkyl groups is a bond or, if located at a terminal position, a hydrogen atom.

As used herein, $C_{1-8}$-alkanoyloxy is $C_{0-7}$-alkylcarbonyloxy such as formyloxy, acetyloxy, n-propionyloxy, isopropionyloxy, n-butyryloxy, isobutyryloxy, sec-butyryloxy and tert-butyryloxy. Examples of $C_{1-8}$-alkyl are methyl, ethyl, n-propyl, isopropyl, n-butyl, isobutyl, sec-butyl, tert-butyl, pentyl and hexyl respectively. Examples of $C_{1-8}$-alkoxy are radicals such as methoxy, ethoxy, n-propoxy, isopropoxy, n-butoxy, isobutoxy, sec-butoxy and tert-butoxy. Examples of $C_{1-8}$-alkoxycarbonylamino are radicals such as methoxycarbonylamino, ethoxycarbonylamino, n-propoxycarbonylamino, iso propoxycarbonylamino, n-butoxycarbonylamino, isobutoxycarbonylamino, secbutoxycarbonylamino and tert-butoxycarbonylamino. Examples of O—$C_{1-8}$-alkylated carboxyl are radicals such as methoxycarbonyl, ethoxycarbonyl, n-propoxycarbonyl, iso propoxycarbonyl, n-butoxycarbonyl, isobutoxycarbonyl, sec-butoxycarbonyl and tert-butoxycarbonyl. Examples of $C_{0-8}$-alkylcarbonylamino are for example formylamino, acetylamino, n-propionylamino, isopropionylamino, n-butylcarbonyl-amino, isobutylcarbonylamino, sec-butylcarbonylamino and tert-butylcarbonylamino. Examples of optionally N-mono- or N,N-di-$C_{1-8}$-alkylated amino are for example methylamino, ethylamino, n-propylamino isopropylamino, n-butylamino, isobutylamino, sec-butylamino, tert-butylamino dimethylamino, diethylamino, di-n-propylamino, diisopropylamino, di-n-butylamino, diisobutylamino, di-sec-butylamino, di-tert-butylamino. Examples of optionally N-mono-, -di- or -tri-$C_{1-8}$-alkylated or heterocyclyl-substituted ureido are radicals such as ureido, 1-methyl-ureido, 3-methyl-ureido, trimethyl-ureido, 1-ethyl-ureido, 3-ethyl-ureido, triethyl-ureido, 1-ethyl-3-methyl-ureido, 3-ethyl-1-methyl-ureido, 1-heterocyclyl-ureido, 3-heterocyclyl-ureido, tri-heterocyclyl-ureido, 1-heterocyclyl-3-methyl-ureido.

The term heterocyclyl refers to 3-8 membered monocyclic, saturated and unsaturated heterocyclic radicals having 1 to 4 nitrogen and/or 1 or 2 sulfur or oxygen atoms, for example optionally substituted, N-bound saturated N-containing $C_{3-8}$-heterocyclyl. The heterocyclyl radicals may be substituted one or more times, such as, for example, substituted once or twice by $C_{1-8}$-alkoxy, $C_{1-8}$-alkyl, optionally esterified carboxy, cyano, halogen, hydroxy, halogen-substituted $C_{1-8}$-alkoxy or halogen-substituted $C_{1-8}$-alkyl.

Examples of such heterocyclyl radicals are imidazolyl, morpholinyl, oxetanyl, oxiranyl, pyrazolyl, pyridyl, pyrrolidinyl, tetrahydrofuranyl, tetrahydropyranyl, tetrazolyl, thiazolyl, triazolyl.

Examples of optionally substituted, N-bound saturated N-containing $C_{3-8}$-heterocyclyl, preferably optionally substituted, N-bound saturated N-containing $C_{5-6}$-heterocyclyl, are optionally substituted pyrrolidinyl or piperidinyl. Preferred substituents on N-bound saturated N-containing heterocyclyl are for example $C_{1-4}$ alkyl, $C_{1-4}$ alkoxy or halogen.

Halogen is fluoro, chloro, bromo or iodo.

Cycloalkyl refers to a saturated cyclic hydrocarbon radicals having 3 to 8 carbon atoms, for example cyclopropyl, cyclobutyl or cyclopentyl and may be unsubstituted or substituted once or twice by $C_{1-8}$-alkoxy, $C_{1-8}$-alkoxy-$C_{1-8}$-alkyl, optionally halogen substituted $C_{1-8}$-alkyl or halogen.

A straight-chain is also sometimes referred to in the literature as linear or unbranched.

Salts are primarily the pharmaceutically acceptable or non-toxic salts of compounds of formula (I). The term "pharmaceutically acceptable salts" encompasses salts with inorganic or organic acids, such as hydrochloric acid, hydrobromic acid, nitric acid, sulfuric acid, phosphoric acid, citric acid, formic acid, maleic acid, acetic acid, succinic acid, tartaric acid, methanesulfonic acid, p-toluenesulfonic acid and the like.

Salts of compounds having salt-forming groups are in particular acid addition salts, salts with bases, or, in the presence of a plurality of salt-forming groups, in some cases also mixed salts or internal salts.

Such salts are formed, for example, from compounds of formula (I) with an acidic group, for example a carboxyl or sulfonyl group, and are, for example, the salts thereof with suitable bases such as non-toxic metal salts derived from metals of group Ia, Ib, IIa and IIb of the Periodic Table of the Elements, for example alkali metal, in particular lithium, sodium, or potassium, salts, alkaline earth metal salts, for example magnesium or calcium salts, and also zinc salts and ammonium salts, including those salts which are formed with organic amines, such as optionally hydroxy-substituted mono-, di- or trialkylamines, in particular mono-, di- or tri (lower alkyl)amines, or with quaternary ammonium bases, e.g. methyl-, ethyl-, diethyl- or triethylamine, mono-, bis- or tris(2-hydroxy(lower alkyl))amines, such as ethanol-, diethanol- or triethanolamine, tris(hydroxymethyl)methylamine or 2-hydroxy-tert-butylamine, N,N-di(lower alkyl)-N-(hydroxy (lower alkyl))amine, such as N,N-di-N-dimethyl-N-(2-hydroxyethyl)amine, or N-methyl-D-glucamine, or quaternary ammonium hydroxides such as tetrabutyl ammoniumhydroxide. The compounds of formula (I) having a basic group, for example an amino group, may form acid addition salts, for example with suitable inorganic acids, e.g. hydrohalic acid such as hydrochloric acid, hydrobromic acid, sulfuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulfonic or phosphonic acids or N-substituted sulfamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, and also amino acids, for example the alpha-amino acids mentioned above, and also methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose 6-phosphate, N-cyclo-hexylsulfamic acid (with formation of the cyclamates) or with other acidic organic compounds such as ascorbic acid. Compounds of formula (I) having acidic and basic groups may also form internal salts.

Salts obtained may be converted to other salts in a manner known per se, acid addition salts, for example, by treating with a suitable metal salt such as a sodium, barium or silver salt, of another acid in a suitable solvent in which an inorganic salt which forms is insoluble and thus separates out of the reaction equilibrium, and base salts by release of the free acid and salt reformation.

The compounds of formula (I), including their salts, may also be obtained in the form of hydrates or include the solvent used for the crystallization.

For the isolation and purification, pharmaceutically unsuitable salts may also find use.

The compounds of formula (I) also include those compounds in which one or more atoms are replaced by their stable, non-radioactive isotopes; for example a hydrogen atom by deuterium.

The compounds of the formula (I) also include compounds that have been nitrosated through one or more sites such as oxygen (hydroxyl condensation) and/or nitrogen. The nitrosated compounds of the present invention can be prepared using conventional methods known to one skilled in the art. For example, known methods for nitrosating compounds are described in WO 2004/098538 A2.

The compounds of the formula (I) also include compounds that have been converted at one or more sites such that a nitrate-ester-containing linker is attached to an existing oxygen and/or nitrogen. Preferred derivatives are compounds where either the piperidine nitrogen atom or a sidechain nitrogen atom in $R^1$ of formula (I) has been converted to either an amide or carbamate group possessing a nitrate-ester-containing linker, for example >N—C(O)-L-$ONO_2$ or >NC(O)—O-L-$ONO_2$, where L represents a linker such as $C_{1-8}$-alkyl or aryl-$C_{1-8}$-alkyl. Further preferred derivatives are compounds where the oxygen atom of a hydroxyl group in $R^1$ of formula (I) has been converted to either an ester or carbonate group possessing a nitrate-ester-containing linker, for example —O—(C=O)-L-$ONO_2$ or —O—(C=C)—O-L-$ONO_2$, where L represents a linker such as $C_{1-8}$-alkyl or aryl-$C_{1-8}$-alkyl. Such "nitroderivatives" of the compounds of the present invention can be prepared using conventional methods known to one skilled in the art. For example, known methods for converting compounds into their nitroderivatives are described in WO 2007/045551 A2.

The compounds of formula (I) have at least four asymmetric carbon atoms and may therefore be in the form of optically pure diastereomers, diastereomeric mixtures, diastereomeric racemates, mixtures of diastereomeric racemates or as meso compounds. The invention encompasses all of these forms. Diastereomeric mixtures, diastereomeric racemates or mixtures of diastereomeric racemates may be separated by customary procedures, for example by column chromatography, thin-layer chromatography, HPLC and the like.

The compounds of formula (I) may also be prepared in optically pure form. The separation into antipodes can be effected by procedures known per se, either preferably at an earlier synthetic stage by salt formation with an optically active acid, for example (+)- or (−)-mandelic acid and separation of the diastereomeric salts by fractional crystallization, or preferably at a relatively late stage by derivatizing with a chiral auxiliary building block, for example (+)- or (−)-camphanoyl chloride, and separation of the diastereomeric products by chromatography and/or crystallization and subsequent cleavage of the bonds to give the chiral auxiliary. The pure diastereomeric salts and derivatives may be analysed to determine the absolute configuration of the piperidine present with common spectroscopic procedures, and X-ray spectroscopy on single crystals constitutes a particularly suitable procedure.

It is possible for the configuration at individual chiral centres in a compound of formula (I) to be inverted selectively. For example, the configuration of asymmetric carbon atoms which bear nucleophilic substituents, such as amino or hydroxyl, may be inverted by second-order nucleophilic substitution, if appropriate after conversion of the bonded nucleophilic substituent to a suitable nucleofugic leaving group and reaction with a reagent which introduces the original substituents, or the configuration at carbon atoms having hydroxyl groups can be inverted by oxidation and reduction, analogously to the process in the European patent application EP-A-0 236 734. Also advantageous is the reactive functional modification of the hydroxyl group and subsequent replacement thereof by hydroxyl with inversion of configuration.

The compound groups mentioned below are not to be regarded as closed, but rather parts of these compound groups may be exchanged with one another or with the definitions given above or omitted in a sensible manner, for example to replace general by more specific definitions. The definitions are valid in accordance with general chemical principles, such as, for example, the common valences for atoms.

The compounds of formula (I) can be prepared in an analogous manner to preparation processes disclosed in the literature. Similar preparation processes are described for example in WO 97/09311. Details of the specific preparation variants can be found in the examples.

A further aspect of the invention are the following intermediates which are closely related to the substituted 4-phenyl piperidines of this invention:
a) (3S,4R,5R)-4-[4-((R)-2-Ethoxy-propoxymethyl)-phenyl]-3-hydroxymethyl-5-[4-(3-methoxy-propyl)-3,4-dihydro-2H-benzo[1,4]oxazin-6-ylmethoxy]-piperidine-1-carboxylic acid tert-butyl ester
and
b) (R)-2-Ethoxy-propan-1-ol A preferred group of compounds of the formula (I) and the salts thereof, preferably the pharmaceutically acceptable salts thereof, are compounds in which
$R^1$ is hydroxyl or hydroxy-substituted $C_{1-8}$-alkyl, more preferably hydroxyl or hydroxy-substituted $C_{1-4}$-alkyl, even more preferably straight-chain omega-hydroxy substituted $C_{1-4}$-alkyl.

A further preferred group of compounds of the formula (I) and the salts thereof, preferably the pharmaceutically acceptable salts thereof, are compounds in which
$R^1$ is $C_{1-8}$-alkoxy, $C_{1-8}$-alkoxy-$C_{1-8}$-alkyl or $C_{1-8}$-alkoxy-$C_{1-8}$-alkoxy, more preferably $C_{1-4}$-alkoxy, $C_{1-4}$-alkoxy-$C_{1-4}$-alkyl or $C_{1-4}$-alkoxy-$C_{1-4}$-alkoxy, even more preferably straight-chain $C_{1-4}$-alkoxy, straight-chain $C_{1-4}$-alkoxy-straight-chain $C_{1-4}$-alkyl or straight-chain $C_{1-4}$-alkoxy-straight-chain $C_{1-4}$-alkoxy, most preferably straight-chain $C_{1-4}$-alkoxy or straight-chain $C_{1-4}$-alkoxy-straight-chain $C_{1-4}$-alkoxy.

A further preferred group of compounds of the formula (I) and the salts thereof, preferably the pharmaceutically acceptable salts thereof, are compounds in which
$R^1$ is $C_{1-8}$-alkanoyloxy or $C_{1-8}$-alkanoyloxy-$C_{1-8}$-alkyl, more preferably $C_{1-4}$-alkanoyloxy or $C_{1-4}$-alkanoyloxy-$C_{1-4}$-alkyl, even more preferably straight-chain $C_{1-4}$-alkanoyloxy.

A further preferred group of compounds of the formula (I) and the salts thereof, preferably the pharmaceutically acceptable salts thereof, are compounds in which
$R^1$ is $C_{0-8}$-alkylcarbonylamino or $C_{0-8}$-alkylcarbonylamino-$C_{1-8}$-alkyl, more preferably $C_{0-3}$-alkylcarbonylamino or $C_{0-3}$-alkylcarbonylamino-$C_{1-4}$-alkyl, even more preferably straight-chain $C_{0-3}$-alkylcarbonylamino.

A further preferred group of compounds of the formula (I) and the salts thereof, preferably the pharmaceutically acceptable salts thereof, are compounds in which
$R^1$ is optionally N-mono- or N,N-di-$C_{1-8}$-alkylated amino or optionally N-mono- or N,N-di-$C_{1-8}$-alkylated amino-$C_{1-8}$-alkyl, more preferably optionally N-mono- or N,N-di-$C_{1-4}$-alkylated amino or optionally N-mono- or N,N-di-$C_{1-4}$-alkylated amino-$C_{1-4}$-alkyl, even more preferably optionally N-mono- or N,N-di-$C_{1-4}$-alkylated amino.

A further preferred group of compounds of the formula (I) and the salts thereof, preferably the pharmaceutically acceptable salts thereof, are compounds in which $R^1$ is optionally substituted heterocyclyl, more preferably optionally substituted N-bound saturated N-containing $C_{3-8}$-heterocyclyl, particularly preferably optionally substituted N-bound saturated N-containing $C_{5-6}$-heterocyclyl.

A further preferred group of compounds of the formula (I) and the salts thereof, preferably the pharmaceutically acceptable salts thereof, are compounds in which $R^1$ is hydroxy, hydroxy-$C_{1-2}$-alkyl, $C_{1-2}$-alkoxy, 2-methoxy-ethoxy, acetyloxy, $C_{0-2}$-alkyl-carbonylamino, $C_{0-2}$-monoalkylamino, N-bound pyrrolidinyl, N-bound piperidinyl or N-bound pyrrolidinyl-carbonyl-$C_{1-2}$-alkyl.

$R^1$ is very particularly preferably hydroxy, methoxy, 2-methoxy-ethoxy, acetyloxy, $C_{0-2}$-alkylcarbonylamino, $C_{1-2}$-monoalkylamino, N-bound pyrrolidinyl or N-bound piperidinyl.

Prodrug derivatives of the compounds described herein are derivatives thereof which on in vivo use liberate the original compound by a chemical or physiological process. A prodrug may for example be converted into the original compound when a physiological pH is reached or by enzymatic conversion. Possible examples of prodrug derivatives are esters of freely available carboxylic acids, S- and O-acyl derivatives of thiols, alcohols or phenols, the acyl group being defined as herein. Preferred derivatives are pharmaceutically acceptable ester derivatives which are converted by solvolysis in physiological medium into the original carboxylic acid, such as, for example, lower alkyl esters, cycloalkyl esters, lower alkenyl esters, benzyl esters, mono- or disubstituted lower alkyl esters such as lower omega-(amino, mono- or dialkylamino, carboxy, lower alkoxycarbonyl)—alkyl esters or such as lower alpha-(alkanoyloxy, alkoxycarbonyl or dialkylaminocarbonyl)—alkyl esters; conventionally, pivaloyloxymethyl esters and similar esters are used as such.

Because of the close relationship between a free compound, a prodrug derivative and a salt compound, a particular compound in this invention also includes its prodrug derivative and salt form, where this is possible and appropriate.

The compounds of formula (I) and their pharmaceutically acceptable salts have an inhibitory effect on the natural enzyme renin. The latter passes from the kidneys into the blood and there brings about the cleavage of angiotensinogen to form the decapeptide angiotensin I which is then cleaved in the lung, the kidneys and other organs to the octapeptide angiotensin II. Angiotensin II raises the blood pressure both directly by arterial constriction, and indirectly by releasing the hormone aldosterone, which retains sodium ions, from the adrenals, which is associated with an increase in the extracellular fluid volume. This increase is attributable to the effect of angiotensin II itself or of the heptapeptide angiotensin III formed therefrom as cleavage product. Inhibitors of the enzymatic activity of renin bring about a reduction in the formation of angiotensin I and, as a consequence thereof, the formation of a smaller amount of angiotensin II. The reduced concentration of this active peptide hormone is the direct cause of the blood pressure-lowering effect of renin inhibitors.

The effect of renin inhibitors is detected inter alia experimentally by means of in vitro tests where the reduction in the formation of angiotensin I is measured in various systems (human plasma, purified human renin together with synthetic or natural renin substrate). The following in vitro test of Nussberger et al. (1987) J. Cardiovascular Pharmacol., Vol. 9, pp. 39-44, is used inter alia. This test measures the formation of angiotensin I in human plasma. The amount of angiotensin I formed is determined in a subsequent radioimmunoassay. The effect of inhibitors on the formation of angiotensin I is tested in this system by adding various concentrations of these substances. The $IC_{50}$ is defined as the concentration of the particular inhibitor which reduces the formation of angiotensin I by 50%. The compounds of the present invention show inhibitory effects in the in vitro systems at minimal concentrations of about $10^{-6}$ to about $10^{-10}$ mol/l.

Illustrative of the invention, the compounds of examples 1 and 2 inhibit the formation of angiotensin I with $IC_{50}$ values in the range of about $0.1-100 \cdot 10^{-9}$ mol/l.

Renin inhibitors bring about a fall in blood pressure in salt-depleted animals. Human renin differs from renin of other species. Inhibitors of human renin are tested using primates (marmosets, *Callithrix jacchus*) because human renin and primate renin are substantially homologous in the enzymatically active region. The following in vivo test is employed inter alia: the test compounds are tested on normotensive marmosets of both sexes with a body weight of about 350 g, which are conscious, unrestrained and in their normal cages. Blood pressure and heart rate are measured with a catheter in the descending aorta and are recorded radiometrically. Endogenous release of renin is stimulated by combining a low-salt diet for 1 week with a single intramuscular injection of furosemide (5-(aminosulfonyl)-4-chloro-2-[(2-furanylmethyl)amino]benzoic acid) (5 mg/kg). 16 h after the furosemide injection, the test substances are administered either directly into the femoral artery by means of a hypodermic needle or as suspension or solution by gavage into the stomach, and their effect on blood pressure and heart rate is evaluated. The compounds of the present invention have a blood pressure-lowering effect in the described in vivo test with i.v. doses of about 0.003 to about 0.3 mg/kg and with oral doses of about 0.3 to about 30 mg/kg.

The blood pressure-reducing effect of the compounds described herein can be tested in vivo using the following protocol:

The investigations take place in 5 to 6-week old, male double transgenic rats (dTGR), which overexpress both human angiotensinogen and human renin and consequently develop hypertension (Bohlender J. et al., J. Am. Soc. Nephrol. 2000; 11: 2056-2061). This double transgenic rat strain was produced by crossbreeding two transgenic strains, one for human angiotensinogen with the endogenous promoter and one for human renin with the endogenous promoter. Neither single transgenic strain was hypertensive. The double transgenic rats, both males and females, develop severe hypertension (mean systolic pressure, approximately 200 mm Hg) and die after a median of 55 days if untreated. The fact that human renin can be studied in the rat is a unique feature of this model. Age-matched Sprague-Dawley rats serve as non-hypertensive control animals. The animals are divided into treatment groups and receive test substance or vehicle (control) for various treatment durations. The applied doses for oral administration may range from 0.5 to 100 mg/kg body weight. Throughout the study, the animals receive standard feed and tap water ad libitum. The systolic and diastolic blood pressure, and the heart rate are measured telemetrically by means of transducers implanted in the abdominal aorta, allowing the animals free and unrestricted movement.

The effect of the compounds described herein on kidney damage (proteinuria) can be tested in vivo using the following protocol:

The investigations take place in 4-week old, male double transgenic rats (dTGR), as described above. The animals are divided into treatment groups and receive test substance or vehicle (control) each day for 7 weeks. The applied doses for oral administration may range from 0.5 to 100 mg/kg body weight. Throughout the study, the animals receive standard feed and tap water ad libitum. The animals are placed periodically in metabolism cages in order to determine the 24-hour urinary excretion of albumin, diuresis, natriuresis, and urine osmolality. At the end of the study, the animals are sacrificed and the kidneys and hearts may also be removed for determining the weight and for immunohistological investigations (fibrosis, macrophage/T cell infiltration, etc.).

The bioavailability of the compounds described herein can be tested in vivo using the following protocol:

The investigations take place in pre-catheterized (carotid artery) male rats (300 g±20%) that can move freely throughout the study. The compound is administered intravenously and orally (gavage) in separate sets of animals. The applied doses for oral administration may range from 0.5 to 50 mg/kg body weight; the doses for intravenous administration may range from 0.5 to 20 mg/kg body weight. Blood samples are collected through the catheter before compound administration and over the subsequent 24-hour period using an automated sampling device (AccuSampler, DiLab Europe, Lund, Sweden). Plasma levels of the compound are determined using a validated LC-MS analytical method. The pharmacokinetic analysis is performed on the plasma concentration-time curves after averaging all plasma concentrations across time points for each route of administration. Typical pharmacokinetics parameters to be calculated include: maximum concentration ($C_{max}$), time to maximum concentration ($t_{max}$), area under the curve from 0 hours to the time point of the last quantifiable concentration ($AUC_{0-t}$), area under the curve from time 0 to infinity ($AUC_{0-inf}$), elimination rate constant (K), terminal half-life ($t_{1/2}$), absolute oral bioavailability or fraction absorbed (F), clearance (CL), and Volume of distribution during the terminal phase (Vd).

Five major metabolizing CYP450 enzymes CYP1A2, CYP2C9, CYP2C19, CYP2D6, and CYP3A4 are responsible for more than 95% of the drug metabolizing activity in humans.

The goals in evaluating in vitro drug metabolism are:
(1) to identify all of the major metabolic pathways that affect the test compound and its metabolites, including the identification of the specific enzymes responsible for metabolism and elucidation of the intermediates formed; and
(2) to explore and anticipate the effects of the test drug on the metabolism of other drugs and the effects of other drugs on its metabolism.

The most complete picture for hepatic metabolism can be obtained with intact liver systems (e.g. hepatocytes, microsomes), in which the cofactors are self-sufficient and the natural orientation and location for linked enzymes is preserved. However, when many compounds have to be tested simultaneously, a simpler screening tool is advantageous. The cDNAs for the common CYP450s have been cloned and the recombinant human enzymatic proteins have been expressed in a variety of cells. Use of these recombinant enzymes provides an excellent way to quickly assess specific enzyme inhibition activities and/or confirm results identified in microsomes.

The metabolic properties (inhibition constants on human cytochrome P450 isoforms) of the compounds described herein can be tested in vivo using the following protocol:

To assess the inhibitory activity towards CYP450 enzymes, the enzymatic reaction is monitored in the presence of different concentrations of test compound (serial dilution) and compared to maximal enzyme activity (control: no test compound). In principle, inhibition can occur by three different mechanisms: (1) competitive inhibition, (2) non-competitive inhibition, and (3) mechanism-based inhibition. In any case, the inhibition strength is dependent on the concentration of test compound. Testing the CYP450 enzyme activity over a test compound concentration range identifies the test compound concentration at which half maximal enzyme inhibition is observed ($IC_{50}$ concentration).

For screening purposes, the inhibitory potential of a test compound can be tested with ready to use kits (CYP450 High Throughput Inhibitor Screening kit, e.g. CYP1A2/CEC, #459500, BD Biosciences, Franklin Lakes, N.J. USA), which are available for all of the five above-mentioned major CYP isoforms. In such kits, recombinant human CYP450 isoforms expressed in insect cells are incubated with isoform specific, fluorogenic substrates in the presence of different test compound concentrations. Enzymatic activity converts the fluorogenic substrate into a fluorochrome product, the concentration of which is measured with a fluoro-spectrophotometer. Fluorescence is directly proportional to enzyme activity.

In a typical standard assay using the CYP450 High Throughput Inhibitor Screening kit, a compound is tested at 2 nM to 33 µM concentration range in a phosphate buffer (50 mM, pH 7.4) containing a glucose 6-phosphate dehydrogenase/NADP/NADPH regeneration system and a suitable fluorogenic substrate: e.g. 3-cyano-7-ethoxycoumarin (CYP1A2). As control inhibitors, the following substances can be used: furafylline (CYP1A2), sulfaphenazole (CYP2C9), tranylcypromine (CYP2C19), quinidine (CYP2D6) and ketoconazole (CYP3A4).

The reaction is started by the addition of 2.5 nM (final concentration) CYP450 isozyme, incubated at 37° C. for 15 to 45 minutes, and then terminated by the addition of 187.5 mM tris-hydroxy-aminomethane base/acetonitrile (20/80, v/v).

The amount of generated fluorochrome is then determined by fluorescence spectroscopy with suitable exitation and emission wavelength settings: e.g. 410 nm excitation and 460 nm emission wavelength (CYP1A2).

Alternatively and/or complimentary, assays using human liver microsomes (e.g. BD Biosciences, #452161) in combination with a CYP isoform-specific standard substrate (e.g. midazolam for CYP3A4/5) as described by R. L. Walsky and R. S. Obach in *Validated assay for human cytochrome p450 activities*; Pharmacokinetics, Pharmacodynamics, and Drug Metabolism, Pfizer, Groton, Conn.; Drug Metabolism and Disposition: (2004)32, 647-660, can be used. To determine whether a test compound inhibits CYP3A enzyme activity, for example, hydroxylation of midazolam by human liver microsomes at varying test compound concentrations is monitored. Hydroxy-midazolam production is directly proportional to enzyme activity and can be determined by liquid chromatography-tandem mass spectrometry. Additionally, the microsomal assay can be run without and with a 15 min pre-incubation of microsomes with test compound prior to the addition of standard substrate. Test compounds or their metabolite(s) that have the potential to irreversibly modify the P450 enzyme will have a stronger inhibitory effect after preincubation.

In a typical standard assay using the human liver microsome assay, compounds are tested at 10 nM to 50 µM concentration range in a phosphate buffer (100 mM potassium phosphate, 3.3 mM $MgCl_2$, pH 7.4) containing a NADPH regeneration system (glucose 6-phosphate dehydrogenase, NADP, NADPH) and 10 µM substrate (e.g. midazolam for CYP3A4/5) and 0.1 mg/mL microsomal protein. As control inhibitors, the same substances as described above can be used (e.g. ketoconazole (CYP3A4/5)). If pre-incubation of the compound is desired, all assay components except substrate are mixed and incubated for 15 minutes at 37° C. After that period, substrate is added to the assay mix and then incubation at 37° C. is continued for 15 minutes. Without pre-incubation, all assay components are mixed simultaneously and then incubated at 37° C. for 15 minutes. Termination of the enzymatic reaction is achieved by the addition of a $HCOOH/acetonitrile/H_2O$ (Apr. 30, 1966, v/v/v) solution. Samples are then incubated in the refrigerator (4±2° C.) for 1 h±10 min to increase protein precipitation. Directly before analysis by LC/MSMS, the samples are centrifuged at 3,500 g for 60 min at 4° C. to separate precipitated protein. The supernatant is mixed with acetonitrile/water (50/50, v/v), and then directly analyzed for compound content with LC/MSMS.

Evaluation of the data from either experimental setup is then done as follows: the fraction of remaining activity at a specific compound concentration versus the activity in the control as a function of compound concentration is used to compute $IC_{50}$ values. This is done by fitting a 4-parameter logistic function to the experimental data set.

The compounds of the formula (I) and their pharmaceutically acceptable salts can be used as medicines, e.g. in the form of pharmaceutical compositions. The pharmaceutical compositions can be administered enterally, such as orally, e.g. in the form of tablets, lacquered tablets, sugar-coated tablets, hard and soft gelatine capsules, solutions, emulsions or suspensions, nasally, e.g. in the form of nasal sprays, rectally, e.g. in the form of suppositories, or transdermally, e.g. in the form of ointments or patches, ophtalmologically, e.g. in the form of solutions, suspensions, ointments, gels, pulmonary, e.g. in the form of pulmonary aerosols or to other mucosal tissues. However, administration is also possible parenterally, such as intramuscularly or intravenously, e.g. in the form of solutions for injection.

Tablets, lacquered tablets, sugar-coated tablets and hard gelatine capsules can be produced by processing the compounds of the formula (I) and their pharmaceutically acceptable salts with pharmaceutically inert inorganic or organic excipients. Excipients of these types which can be used for example for tablets, sugar-coated tablets and hard gelatine capsules are lactose, maize starch or derivatives thereof, talc, stearic acid or salts thereof etc.

Excipients suitable for soft gelatine capsules are, for example, vegetable oils, waxes, fats, semisolid and liquid polyols etc.

Excipients suitable for producing solutions and syrups are, for example, water, polyols, sucrose, invert sugar, glucose etc.

Excipients suitable for solutions for injection are, for example, water, alcohols, polyols, glycerol, vegetable oils, bile acids, lecithin etc.

Excipients suitable for suppositories are, for example, natural or hardened oils, waxes, fats, semiliquid or liquid polyols etc.

The pharmaceutical compositions may in addition comprise preservatives, solubilizers, viscosity-increasing substances, stabilizers, wetting agents, emulsifiers, sweeteners, colorants, aromatizers, salts to alter the osmotic pressure, buffers, coating agents or antioxidants. They may also comprise other substances of therapeutic value.

The present invention further provides the use of the compounds of the formula (I) and their pharmaceutically acceptable salts in the treatment or prevention of high blood pressure, heart failure, glaucoma, myocardial infarction, renal failure, diabetic nephropathy and restenoses.

The compounds of the formula (I) and their pharmaceutically acceptable salts can also be administered in combination with one or more agents having cardiovascular activity, e.g. alpha- and beta-blockers such as phentolamine, phenoxybenzamine, prazosin, terazosin, tolazine, atenolol, metoprolol, nadolol, propranolol, timolol, carteolol etc.; vasodilators such as hydralazine, minoxidil, diazoxide, nitroprusside, flosequinan etc.; calcium antagonists such as aminone, bencyclan, diltiazem, fendiline, flunarizine, nicardipine, nimodipine, perhexyline, verapamil, gallopamil, nifedipine etc.; ACE inhibitors such as cilazapril, captopril, enalapril, lisinopril etc.; potassium activators such as pinacidil; antiserotoninergics such as ketanserine; thromboxane synthetase inhibitors; neutral endopeptidase inhibitors (NEP inhibitors); angiotensin II antagonists; and diuretics such as hydrochlorothiazide, chlorothiazide, acetazolamide, amiloride, bumetanide, benzthiazide, ethacrynic acid, furosemide, indacrinone, metolazone, spironolactone, triamterene, chlorthalidone etc.; sympatholytics such as methyldopa, clonidine, guanabenz, reserpine; and other agents suitable for the treatment of high blood pressure, heart failure or vascular disorders associated with diabetes or renal disorders such as acute or chronic renal failure in humans and animals. Such combinations can be used separately or in products which comprise a plurality of components.

Further substances which can be used in combination with the compounds of formula (I) are the compounds of classes (i) to (ix) on page 1 of WO 02/40007 (and the preferences and examples detailed further therein) and the substances mentioned on pages 20 and 21 of WO 03/027091.

The dosage may vary within wide limits and must of course be adapted to the individual circumstances in each individual case. In general, a daily dose appropriate for oral administration ought to be from about 3 mg to about 3 g, preferably about 10 mg to about 1 g, e.g. approximately 300 mg per adult person (70 kg), divided into preferably 1-3 single doses, which may be for example of equal size, although the stated upper limit may also be exceeded if this proves to be indicated, and children usually receive a reduced dose appropriate for their age and body weight.

The compounds of the formula (I) and their pharmaceutically acceptable salts can also be administered with one or several varying dosing intervals, as long as the intended therapeutic effect is sustained or as long as further therapeutic intervention is not required.

EXAMPLES

The following examples illustrate the present invention. All temperatures are stated in degrees Celsius and pressures in mbar. Unless mentioned otherwise, the reactions take place at RT. The abbreviation "Rf=xx (A)" means for example that the Rf is found in solvent system A to be xx. The ratio of amounts of solvents to one another is always stated in parts by volume. Chemical names for final products and intermediates have been generated on the basis of the chemical structural formulae with the aid of the AutoNom 2000 (Automatic Nomenclature) program.

Thin-film chromatography eluent systems:

A dichloromethane-methanol-25% ammonia conc.=200:20:1

B dichloromethane-methanol-25% ammonia conc.=200:10:1

C dichloromethane-methanol-25% ammonia conc.=200:30:1

D dichloromethane-methanol-25% ammonia conc.=100:10:1

| HPLC gradients on Hypersil BDS C-18 (5 um); column: 4 × 125 mm |
|---|
| I  90% water*/10% acetonitrile* to 0% water*/100% acetonitrile* in 5 minutes + 2.5 minutes (1.5 ml/min) |
| II  95% water*/5% acetonitrile* to 0% water*/100% acetonitrile* in 30 minutes + 5 minutes (0.8 ml/min) |

*contains 0.1% trifluoroacetic acid

The following abbreviations are used:

| | |
|---|---|
| AcOH | acetic acid |
| n-BuLi | n-butyllithium |
| t-BuOH | tert-butanol |
| $CH_2Cl_2$ | dichloromethane |
| $CHCl_3$ | chloroform |
| $CH_3CN$ | acetonitrile |
| Cy | cyclohexane |
| DCC | dicyclohexylcarbodiimide |
| DIBAL | diisobutylaluminium hydride |
| DME | 1,2-dimethoxyethane |
| DMF | N,N-dimethylformamide |
| EDC•HCl | N-ethyl-N'-(3-dimethylaminopropyl)carbodiimide hydrochloride [25952-53-8] |
| $Et_3N$ | triethylamine |
| $Et_2O$ | diethylether |
| EtOAc | ethyl acetate |
| EtOH | ethanol |
| h | hour(s) |
| HBr | hydrobromic acid |
| HCl | hydrochloric acid |
| $H_2O$ | water |
| $K_2CO_3$ | potassium carbonate |
| $KHSO_4$ | potassium bisulfate solution |
| LiCl | lithium chloride |
| MeI | methyl iodide |
| MeOH | methanol |
| min | minute(s) |
| m.p. | melting point (temperature) |
| $N_2$ | nitrogen |
| $Na_2CO_3$ | sodium carbonate |
| NaH | sodium hydride |
| $NaHCO_3$ | sodium bicarbonate |
| $NaOCH_3$ | sodium methoxide |
| NaOH | sodium hydroxide |
| $Na_2SO_4$ | sodium sulfate |
| $NH_3$ | ammonia |
| $NH_4Br$ | ammonium bromide |
| $NH_4Cl$ | ammonium chloride |
| $NH_4OH$ | ammonium hydroxide |
| $Pd_2(dba)_3$ | tris(dibenzylideneacetone)dipalladium [51364-51-3] |
| $Pd(PPh_3)_4$ | tetrakis-triphenylphosphine palladium(0) |
| $P(tert-Bu)_3$ | tri-tert-butylphosphine |
| Ra/Ni | Raney-nickel |
| Rf | ratio of distance which a substance travels to distance of the eluent front from the start point in thin layer chromatography |
| Rt | retention time of a substance in HPLC (in minutes) |
| RT | room temperature |
| TBME | tert-butyl methyl ether |
| TFA | trifluoroacetic acid |
| THF | tetrahydrofuran |

General Method A: (N—BOC Deprotection)

20 mmol of TFA are added to a solution of 1 mmol of "N—BOC derivative" in 6 ml of $CH_2Cl_2$ under argon at 0° C. After stirring for 2-8 h, the reaction mixture is slowly transferred via cannula into an ice-cold 1M aqueous $NaHCO_3$ solution. After stirring for 30 min, the phases are separated. The aqueous phase is extracted with $CH_2Cl_2$ (2×)—the combined organic phases are washed successively with ice-cold 1M aqueous $NaHCO_3$ solution and brine, dried over $Na_2SO_4$ and concentrated by evaporation. The title compound is obtained from the residue by means of flash chromatography ($SiO_2$ 60F).

General Method B: (Hydrogenation)

The solution of 1 mmol of "substrate" in 15 ml of MeOH is hydrogenated in the presence of 100-200 mg of 10% Pd/C at 15-20° C. over 2-20 h. The reaction mixture is clarified by filtration and the filtrate is concentrated by evaporation. The title compound is obtained from the residue by means of flash chromatography ($SiO_2$ 60F).

General Method C: (O-alkylation I)

1.2 mmol mmol of NaH (60% dispersion in oil) and 0.1 mmol of tetrabutylammonium iodide are added to a solution of 1 mmol of "alcohol" and 1.1 mmol of "benzyl halide" in 2.0 ml of DMF while stirring at −10° C. The reaction mixture is stirred at −10° C. for 1 h and at RT for 18 h. The mixture is poured into 1M aqueous $NaHCO_3$ solution and extracted with TBME (2×). The organic phases are washed successively with $H_2O$ and brine, dried over $Na_2SO_4$ and evaporated. The title compound is obtained from the residue by means of flash chromatography ($SiO_2$ 60F).

General Method G: (Tosylation)

A solution of 12 mmol of p-toluenesulfonyl chloride in 15 ml of $CH_2Cl_2$ is added dropwise at 0° C. to the solution of 10 mmol of "alcohol", 15 mmol of $Et_3N$, 1 mmol of 4-dimethylaminopyridine in 90 ml of $CH_2Cl_2$. The reaction mixture is stirred at RT over 2-18 h. The reaction mixture is diluted with dichloromethane and subsequently washed with $H_2O$ and brine, dried over $Na_2SO_4$ and concentrated by evaporation. The title compound is obtained from the residue by means of flash chromatography ($SiO_2$ 60F).

General Method J: ($BH_3$ Reduction)

A solution of 1 mmol of "substrate" in 3 ml of THF is mixed with 2.0-6.0 mmol of borane-tetrahydrofuran complex (1M in THF) and stirred at RT for 1-3 h (conversion checked by HPLC or TLC). The reaction mixture is mixed with 3.0-6.0 mmol of MeOH and evaporated. The title compound is obtained from the residue by flash chromatography ($SiO_2$ 60F).

General Method L: (Hydrogenation)

To a stirred solution of 1 mmol of "substrate" in 15 ml of MeOH are added 100-200 mg Pd/C 10% and the reaction mixture is hydrogenated at 15-20° C. The reaction mixture is filtered and concentrated under reduced pressure. The residue is purified by flash chromatography ($SiO_2$ 60F) to afford the title compound.

General Method N (Alcohol Desilylation)

A solution of 1 mmol of "silyl ether" in 5 ml of THF is mixed with 1.5-2.0 mmol of tetrabutylammonium fluoride (1M solution in THF), and the solution is stirred at RT for 1-2 h. The reaction solution is then diluted with $H_2O$ and extracted with TBME (2×). The combined organic phases are dried over $Na_2SO_4$ and evaporated. The title compound is obtained from the residue by flash chromatography ($SiO_2$ 60F).

Example 1

{(3S,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-piperidin-3-yl}-methanol According to general method A, 1 mmol of (3S,4R,5R)-4-[4-((R)-2-ethoxy-propoxymethyl)-phenyl]-3-hydroxymethyl-5-[4-(3-methoxy-propyl)-3,4-dihydro-2H-benzo[1,4]oxazin-6-ylmethoxy]-piperidine-1-carboxylic acid tert-butyl ester are used to provide the title compound, which is identified based on the Rf value.

The starting material(s) is (are) prepared as follows:
a) (3S,4R,5R)-4-[4-((R)-2-Ethoxy-propoxymethyl)-phenyl]-3-hydroxymethyl-5-[4-(3-methoxy-propyl)-3,4-dihydro-2H-benzo[1,4]oxazin-6-ylmethoxy]-piperidine-1-carboxylic acid tert-butyl ester According to general method N, 0.95 mmol of (3R,4R,5S)-4-[4-((R)-2-ethoxy-propoxymethyl)-phenyl]-3-[4-(3-methoxy-propyl)-3,4-dihydro-2H-benzo[1,4]oxazin-6-ylmethoxy]-5-triisopropylsilanyloxymethyl-piperidine-1-carboxylic acid tert-butyl ester are used to provide the crude title compound as a yellow oil. Rf=0.06 (EtOAc/heptane 1:1); Rt=5.10 (gradient I).
b) (3R,4R,5S)-4-[4-((R)-2-Ethoxy-propoxymethyl)-phenyl]-3-[4-(3-methoxy-propyl)-3,4-dihydro-2H-benzo[1,4]oxazin-6-ylmethoxy]-5-triisopropylsilanyloxymethyl-piperidine-1-carboxylic acid tert-butyl ester According to general method C, 1.25 mmol of (3R,4R,5S)-4-(4-chloromethyl-phenyl)-3-[4-(3-methoxy-propyl)-3,4-dihydro-2H-benzo[1,4]oxazin-6-ylmethoxy]-5-triisopropylsilanyloxymethyl-piperidine-1-carboxylic acid tert-butyl ester and 1.57 mmol of (R)-2-ethoxy-propan-1-ol are used to provide the title compound as a light yellow oil. Rf=0.38 (EtOAc/heptane 1:1).
c) (3R,4R,5S)-4-(4-Chloromethyl-phenyl)-3-[4-(3-methoxy-propyl)-3,4-dihydro-2H-benzo[1,4]oxazin-6-ylmethoxy]-5-triisopropylsilanyloxymethyl-piperidine-1-carboxylic acid tert-butyl ester 1.32 mmol of methanesulfonyl chloride are added to a mixture of 1.23 mmol of (3R,4R,5S)-4-(4-hydroxymethyl-phenyl)-3-[4-(3-methoxy-propyl)-3,4-dihydro-2H-benzo[1,4]oxazin-6-ylmethoxy]-5-triisopropylsilanyloxymethyl-piperidine-1-carboxylic acid tert-butyl ester, 1.45 mmol of $Et_3N$ and 0.086 mmol of tetrabutylammonium chloride in 10 ml of $CH_2Cl_2$ at RT. After 16 h, the reaction mixture is diluted with $CH_2Cl_2$ and washed successively with saturated aqueous $NaHCO_3$ and brine. The combined aqueous phases are extracted with $CH_2Cl_2$—the combined organic phases are dried over $Na_2SO_4$ and concentrated by evaporation. The crude title compound is obtained as a brown-orange oil. Rf=0.40 (EtOAc/heptane 1:1).
d) (3R,4R,5S)-4-(4-Hydroxymethyl-phenyl)-3-[4-(3-methoxy-propyl)-3,4-dihydro-2H-benzo[1,4]oxazin-6-ylmethoxy]-5-triisopropylsilanyloxymethyl-piperidine-1-carboxylic acid tert-butyl ester According to general method J, 1 mmol of (3R,4R,5S)-4-(4-carboxy-phenyl)-3-[4-(3-methoxy-propyl)-3-oxo-3,4-dihydro-2H-benzo[1,4]oxazin-6-ylmethoxy]-5-triisopropylsilanyloxymethyl-piperidine-1-carboxylic acid tert-butyl ester are used to provide the title compound as a viscous yellow-brown oil. Rf=0.20 (EtOAc/heptane 1:1); Rt=31.34 (gradient II).
e) (3R,4R,5S)-4-(4-Carboxy-phenyl)-3-[4-(3-methoxy-propyl)-3-oxo-3,4-dihydro-2H-benzo[1,4]oxazin-6-ylmethoxy]-5-triisopropylsilanyloxymethyl-piperidine-1-carboxylic acid tert-butyl ester 4.30 mmol of NaOH are added to a solution of 1.05 mmol of (3R,4R,5S)-4-(4-methoxycarbonyl-phenyl)-3-[4-(3-methoxy-propyl)-3-oxo-3,4-dihydro-2H-benzo[1,4]oxazin-6-ylmethoxy]-5-triisopropylsilanyloxymethyl-piperidine-1-carboxylic acid tert-butyl ester in 10 ml of THF and 10 ml of H₂O. The resulting reaction mixture is stirred at 90° C. for 16 h and then cooled to RT. After dilution with H₂O and acidification (pH 3) with 4N aqueous HCl, the mixture is extracted with TBME (2×)—the combined organic phases are washed with brine, dried over Na₂SO₄ and concentrated by evaporation. The crude title compound is obtained as a viscous brown oil. Rf=0.24 (EtOAc/heptane 2:1+a drop of formic acid); Rt=6.71 (gradient I).

f) (3R,4R,5S)-4-(4-Methoxycarbonyl-phenyl)-3-[4-(3-methoxy-propyl)-3-oxo-3,4-dihydro-2H-benzo[1,4]oxazin-6-ylmethoxy]-5-triisopropylsilanyloxymethyl-piperidine-1-carboxylic acid tert-butyl ester According to general method C, 1.14 mmol of (3R,4R,5S)-3-hydroxy-4-(4-methoxy-carbonyl-phenyl)-5-triisopropylsilanyloxymethyl-piperidine-1-carboxylic acid tert-butyl ester and 1.20 mmol of 6-bromomethyl-4-(3-methoxy-propyl)-4H-benzo[1,4]oxazin-3-one [911705-42-5] are used to provide the crude title compound as a viscous brown oil. Rf=0.28 (EtOAc/heptane 1:1); Rt=7.33 (gradient I).

g) (3R,4R,5S)-3-Hydroxy-4-(4-methoxycarbonyl-phenyl)-5-triisopropylsilanyloxymethyl-piperidine-1-carboxylic acid tert-butyl ester 2.79 mmol of imidazole and 1.29 mmol of chloro-triisopropyl-silane are added to a solution of 1.03 mmol of (3R,4R,5S)-3-hydroxy-5-hydroxymethyl-4-(4-methoxy-carbonyl-phenyl)-piperidine-1-carboxylic acid tert-butyl ester in 5 ml of DMF. After stirring at RT for 16 h, the reaction mixture is partitioned between TBME and 2N HCl. The organic phase is washed successively with H₂O and brine, dried over Na₂SO₄ and concentrated by evaporation. The title compound is obtained as a colorless oil from the residue by means of flash chromatography (SiO₂ 60F). Rf=0.48 (EtOAc/heptane 1:1); Rt=6.68 (gradient I).

h) (3R,4R,5S)-3-Hydroxy-5-hydroxymethyl-4-(4-methoxycarbonyl-phenyl)-piperidine-1-carboxylic acid tert-butyl ester 155 ml of DMF, 115 ml of MeOH, 2.23 mmol of 1,3-bis(diphenylphosphino)propane and 2.23 mmol of palladium(II) acetate are introduced into an autoclave under argon. The reaction mixture is stirred at RT for 20 min. 48.69 mmol of (3R,4R,5S)-3-hydroxy-5-hydroxymethyl-4-(4-trifluoromethanesulfonyloxy-phenyl)-piperidine-1-carboxylic acid tert-butyl ester and 98.8 mmol of triethylamine are then added and the autoclave is loaded with 5 bar of carbon monoxide. The reaction mixture is then stirred under a pressure of 5 bar at 70° C. for 4 h. After cooling to RT, additional palladium(II) acetate (2.23 mmol) and 1,3-bis(diphenylphosphino)propane (2.23 mmol) are added after 4 h and 8 h respectively and the reaction mixture is then stirred under 5 bar of carbon monoxide at 70° C. The reaction solution is cooled to RT and concentrated by evaporation. The title compound is obtained as a viscous brown oil from the residue by means of flash chromatography (SiO₂ 60F). Rf=0.14 (EtOAc/heptane 2:1); Rt=3.35 (gradient I).

i) (3R,4R,5S)-3-Hydroxy-5-hydroxymethyl-4-(4-trifluoromethanesulfonyloxy-phenyl)-piperidine-1-carboxylic acid tert-butyl ester 61.13 mmol of Et₃N are added dropwise to a mixture of 57.67 mmol of (3R,4R,5S)-3-hydroxy-5-hydroxymethyl-4-(4-hydroxy-phenyl)-piperidine-1-carboxylic acid tert-butyl ester [303043-57-4] and 59.40 mmol of N-phenyltrifluoromethanesulfonimide in 120 ml of CH₂Cl₂ at 0° C. After stirring for 16 h at RT, the reaction mixture is diluted with CH₂Cl₂ and washed successively with 1M aqueous Na₂CO₃ solution and brine. The combined aqueous phases are extracted with CH₂Cl₂—the combined organic phases are dried over Na₂SO₄ and concentrated by evaporation. The title compound is obtained as a pale yellow foam from the residue by means of flash chromatography (SiO₂ 60F). Rf=0.50 (EtOAc/heptane 3:1); Rt=4.42 (gradient I).

j) (R)-2-Ethoxy-propan-1-ol 17.1 mmol of lithium borohydride are added portionwise to a solution of 11.0 mmol of (R)-2-ethoxy-propionic acid methyl ester in 20 ml of Et₂O under Ar at 0° C. After stirring for 1 h at 0° C. and 18 h at RT, the reaction mixture is slowly poured into an ice-cold saturated aqueous NH₄Cl solution. The phases are separated and then the aqueous phase is extracted with CH₂Cl₂ (5×)—the combined organic phases are dried over Na₂SO₄ and concentrated (35° C., 300 mbar) by evaporation. The crude title compound is obtained as a slightly turbid yellow-brown oil. Rf=0.30 (pentane/Et₂O 1:1).

k) (R)-2-Ethoxy-propionic acid methyl ester 28.5 mmol of silver oxide are added to a vigorously stirred solution of 14.25 mmol of methyl-(R)-lactate [17392-83-5] and 28.5 mmol of ethyl iodide in 50 ml of Et₂O under Ar at RT. The reaction flask is wrapped in aluminum foil to exclude light. After 16 h, an additional 14.25 mmol of ethyl iodide and 14.25 mmol of silver oxide are added to the reaction mixture. After 20 h, the reaction is clarified by filtration over Hyflo®, using first Et₂O and then CH₂Cl₂ to wash the filter cake. The combined filtrates are concentrated (35° C., 300 mbar) by evaporation. The title compound is obtained from the residue as a light yellow oil by means of flash chromatography (SiO₂ 60F). Rf=0.35 (pentane/Et₂O 4:1).

Example 2

Acetic acid (3S,4R,5R)-4-[4-((R)-2-ethoxy-propoxymethyl)-phenyl]-5-[4-(3-methoxypropyl)-3,4-dihydro-2H-benzo[1,4]oxazin-6-ylmethoxy]-piperidin-3-ylmethyl ester According to general procedure A, (3S,4R,5R)-3-acetoxymethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester is used to afford the title compound, which is identified based on the Rf value.

The starting material(s) is (are) prepared as follows:

a) (3S,4R,5R)-3-Acetoxymethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester 0.89 mmol of acetyl chloride are added to a solution of 0.81 mmol of (3S,4R,5R)-4-[4-((R)-2-ethoxy-propoxymethyl)-phenyl]-3-hydroxymethyl-5-[4-(3-methoxy-propyl)-3,4-dihydro-2H-benzo[1,4]oxazin-6-ylmethoxy]-piperidine-1-carboxylic acid tert-butyl ester (example 1a) and 0.97 mmol of Et₃N in 7 ml of CH₂Cl₂ under argon at 0° C. After 1 h, the reaction mixture is diluted with CH₂Cl₂ and washed with successively with saturated aqueous NaHCO₃ solution and brine. The combined aqueous phases are extracted with CH₂Cl₂—the combined organic layers are dried over Na₂SO₄ and concentrated by evaporation. The title compound is

Example 3

6-{(3R,4R,5S)-5-Methoxymethyl-4-[4-((R)-2-ethoxy-propoxymethyl)-phenyl]-piperidin-3-yloxymethyl}-4-(3-methoxy-propyl)-3,4-dihydro-2H-benzo[1,4]oxazine According to general procedure A, (3S,4R,5R)-4-[4-((R)-2-ethoxy-propoxymethyl)-phenyl]-3-methoxymethyl-5-[4-(3-methoxy-propyl)-3,4-dihydro-2H-benzo[1,4]oxazin-6-ylmethoxy]-piperidine-1-carboxylic acid tert-butyl ester is used to afford the title compound, which is identified based on the Rf value.

The starting material(s) is (are) prepared as follows:
a) (3S,4R,5R)-4-[4-((R)-2-Ethoxy-propoxymethyl)-phenyl]-3-methoxymethyl-5-[4-(3-methoxy-propyl)-3,4-dihydro-2H-benzo[1,4]oxazin-6-ylmethoxy]-piperidine-1-carboxylic acid tert-butyl ester 2.568 mmol of methyl iodide are added to a suspension of 0.642 mmol of (3S,4R,5R)-4-[4-((R)-2-ethoxy-propoxymethyl)-phenyl]-3-hydroxymethyl-5-[4-(3-methoxy-propyl)-3,4-dihydro-2H-benzo[1,4]oxazin-6-ylmethoxy]-piperidine-1-carboxylic acid tert-butyl ester (example 1a) and 0.963 mmol of NaH (60% dispersion in oil) under argon at 0° C. After stirring for 1 h at 0° C. and 1 h at RT, the reaction mixture is partitioned between TBME and saturated aqueous NaHCO3 solution. The aqueous layer is extracted with TBME (2×)—the combined organic layers are washed successively with $H_2O$ and brine, dried with $Na_2SO_4$ and evaporated. The residue is purified by flash chromatography ($SiO_2$ 60F) to afford the title compound, which is identified based on the Rf value.

According to the procedures described in example 3, the following compound is prepared in an analogous manner:
4  6-[(3R,4R,5S)-4-[4-((R)-2-Ethoxy-Propoxymethyl)-phenyl]-5-(2-methoxy-ethoxymethyl)-piperidin-3-yloxymethyl]-4-(3-methoxy-propyl)-3,4-dihydro-2H-benzo[1,4]oxazine
using 1-bromo-2-methoxy-ethane (instead of methyl iodide) and 1 equivalent of tetrabutylammonium iodide in step a.

Example 5

2-{(3S,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-piperidin-3-yl}-ethanol According to general procedure A, (3S,4R,5R)-4-[4-((R)-2-ethoxy-propoxymethyl)-phenyl]-3-(2-hydroxy-ethyl)-5-[4-(3-methoxy-propyl)-3,4-dihydro-2H-benzo[1,4]oxazin-6-ylmethoxy]-piperidine-1-carboxylic acid tert-butyl ester is used to afford the title compound, which is identified based on the Rf value.

The starting material(s) is (are) prepared as follows:
a) (3S,4R,5R)-4-[4-((R)-2-Ethoxy-propoxymethyl)-phenyl]-3-(2-hydroxy-ethyl)-5-[4-(3-methoxy-propyl)-3,4-dihydro-2H-benzo[1,4]oxazin-6-ylmethoxy]-piperidine-1-carboxylic acid tert-butyl ester According to general procedure J, (3S,4R,5R)-3-carboxymethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester is used to afford the title compound, which is identified based on the Rf value.

b) (3S,4R,5R)-3-Carboxymethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester A solution of 1 mmol of (3S,4R,5R)-3-cyanomethyl-4-[4-((R)-2-ethox-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester in 4 ml of EtOH and 4 ml of 2N NaOH is heated to 85° C. overnight. The reaction mixture is allowed to cool to RT, acidified by addition of 1N HCl solution and extracted with EtOAc. The organic phase is dried over $Na_2SO_4$ and concentrated by evaporation. The residue is purified by flash chromatography ($SiO_2$ 60F) to afford the title compound, which is identified based on the Rf value.

c) (3S,4R,5R)-3-Cyanomethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester To a solution of 1 mmol of (3R,4R,5S)-4-[4-((R)-2-ethoxy-propoxymethyl)-phenyl]-3-[4-(3-methoxy-propyl)-3,4-dihydro-2H-benzo[1,4]oxazin-6-ylmethoxy]-5-(toluene-4-sulfonyloxymethyl)-piperidine-1-carboxylic acid tert-butyl ester in 3 ml of DMSO are added 10 mmol of sodium cyanide and the mixture is heated to 50° C. for 4 h. The reaction mixture is diluted with $H_2O$, extracted with EtOAc, dried over $Na_2SO_4$ and concentrated by evaporation. The residue is purified by flash chromatography ($SiO_2$ 60F) to afford the title compound, which is identified based on the Rf value.

d) (3R,4R,5S)-4-[4-((R)-2-Ethoxy-propoxymethyl)-phenyl]-3-[4-(3-methoxy-propyl)-3,4-dihydro-2H-benzo[1,4]oxazin-6-ylmethoxy]-5-(toluene-4-sulfonyloxymethyl)-piperidine-1-carboxylic acid tert-butyl ester According to general method G, 0.93 mmol of (3S,4R,5R)-4-[4-((R)-2-ethoxy-propoxymethyl)-phenyl]-3-hydroxymethyl-5-[4-(3-methoxy-propyl)-3,4-dihydro-2H-benzo[1,4]oxazin-6-ylmethoxy]-piperidine-1-carboxylic acid tert-butyl ester (example 1a) are used to provide the crude title compound as a yellow-orange oil. Rf=0.20 (EtOAc/heptane 1:1); Rt=5.96 (gradient I).

Example 6

C-{(3R,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-piperidin-3-yl}-methylamine According to general procedure A, (3R,4R,5R)-3-aminomethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester is used to afford the title compound, which is identified based on the Rf value.

The starting material(s) is (are) prepared as follows:
a) (3R,4R,5R)-3-Aminomethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester According to general method L, 0.83 mmol of (3S,4R,5R)-3-azidomethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester are used to provide the crude title compound as a pale yellow oil. Rf=0.03 (CH$_2$Cl$_2$/MeOH/NH$_3$ 200:10:1); Rt=4.51 (gradient I).

b) (3S,4R,5R)-3-Azidomethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester 4.57 mmol of sodium azide are added to a solution of 0.91 mmol of (3R,4R,5S)-4-[4-((R)-2-ethoxy-propoxymethyl)-phenyl]-3-[4-(3-methoxy-propyl)-3,4-dihydro-2H-benzo[1,4]oxazin-6-ylmethoxy]-5-(toluene-4-sulfonyloxymethyl)-piperidine-1-carboxylic acid tert-butyl ester (example 5d) in 5 ml of 1,3-dimethyl-tetrahydro-pyrimidin-2-one (DMPU) under argon at 50° C. After 2 h, the reaction mixture is cooled to RT, diluted with TBME, washed successively with H$_2$O (2×) and brine, dried over Na$_2$SO$_4$ and concentrated by evaporation. The title compound is obtained from the residue by means of flash chromatography (SiO$_2$ 60F) as a pale yellow oil from the residue by means of flash chromatography (SiO$_2$ 60F). Rf=0.27 (EtOAc/heptane 1:1); Rt=5.98 (gradient I).

7 N-{(3S,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-piperidin-3-ylmethyl}-formamide According to general method A, 1.21 mmol of (3R,4R,5R)-4-[4-((R)-2-ethoxy-propoxymethyl)-phenyl]-3-formylaminomethyl-5-[4-(3-methoxy-propyl)-3,4-dihydro-2H-benzo[1,4]oxazin-6-ylmethoxy]-piperidine-1-carboxylic acid tert-butyl ester are used to provide the title compound, which is identified based on the Rf value.

The starting material(s) is (are) prepared as follows:

a) (3R,4R,5R)-4-[4-((R)-2-Ethoxy-propoxymethyl)-phenyl]-3-formylaminomethyl-5-[4-(3-methoxy-propyl)-3,4-dihydro-2H-benzo[1,4]oxazin-6-ylmethoxy]-piperidine-1-carboxylic acid tert-butyl ester 1.4 mmol of 4-nitrophenylformiate are added to a solution of 1 mmol of (3R,4R,5R)-3-aminomethyl-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid benzyl ester (example 6a) in 10 ml of CH$_2$Cl$_2$ under argon followed by the addition of 1 mmol of Et$_3$N. After 60 min, the reaction mixture is evaporated. The residue is purified by flash chromatography (SiO$_2$ 60F) to afford the title compound, which is identified based on the Rf value.

Example 8

N-{(3S,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-piperidin-3-ylmethyl}-acetamide According to general method A, 1.21 mmol of (3R,4R,5R)-3-(acetylamino-methyl)-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester are used to provide the title compound as a viscous dark yellow oil. Rf=0.05 (CH$_2$Cl$_2$/MeOH/NH$_3$ 200:20:1); Rt=3.66 (gradient I).

The starting material(s) is (are) prepared as follows:
a) (3R,4R,5R)-3-(Acetylamino-methyl)-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidine-1-carboxylic acid tert-butyl ester Analogously to example 2a, (3R,4R,5R)-3-aminomethyl-4-[4-((R)-2-ethoxypropoxy-methyl)-phenyl]-5-[4-(3-methoxy-propyl)-3,4-dihydro-2H-benzo[1,4]oxazin-6-ylmethoxy]-piperidine-1-carboxylic acid tert-butyl ester (example 6a) and acetyl chloride are used to afford the title compound as a yellow oil oil from the residue by means of flash chromatography (SiO$_2$ 60F). Rf=0.12 (EtOAc); Rt=4.87 (gradient I).

According to the procedures described in example 8, the following compounds are prepared in an analogous manner:

9 N-{(3S,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-piperidin-3-ylmethyl}-propionamide using propionyl chloride instead of acetyl chloride in step a.

Example 10

{(3R,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-piperidin-3-ylmethyl}-methyl-amine A solution of 1 mmol of N-{(3S,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidin-3-ylmethyl}-formamide (example 7) 8 ml of THF is mixed with 2 mmol of LiAlH$_4$ (1M in THF) and stirred at RT for 13 h (conversion checked by HPLC or TLC), then the reaction mixture is heated to 40° C. for 2 h. The reaction mixture is poured on saturated aqueous NaHCO$_3$ solution and extracted with TBME (3×). The combined organic phases are washed with H$_2$O and brine and evaporated in vacuo. The title compound is obtained from the residue by flash chromatography (SiO$_2$ 60F) and identified based on the Rf value.

According to the procedures described in example 10, the following compound is prepared in an analogous manner:

11 {(3R,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-piperidin-3-ylmethyl}-ethyl-amine starting from N-{(3S,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidin-3-ylmethyl}-acetamide (example 8) instead of N-{(3S,4R,5R)-4-[4-((R)-2-ethoxy-propoxymethyl)-phenyl]-5-[4-(3-methoxy-propyl)-3,4-dihydro-2H-benzo[1,4]oxazin-6-ylmethoxy]-piperidin-3-ylmethyl}-formamide (example 7).

Example 12

6-{(3R,4R,5S)-4-[4-((R)-2-Ethoxy-propoxymethyl)-phenyl]-5-pyrrolidin-1-ylmethyl-piperidin-3-yloxymethyl}-4-(3-methoxy-propyl)-3,4-dihydro-2H-benzo[1,4]oxazine According to general method A, 1.21 mmol of (3R,4R,5R)-4-[4-((R)-2-ethoxy-propoxymethyl)-phenyl]-3-[4-(3-methoxy-propyl)-3,4-dihydro-2H-benzo[1,4]oxazin-6-ylmethoxy]-5-pyrrolidin-1-ylmethyl-piperidine-1-carboxylic acid tert-butyl ester are used to provide the title compound, which is identified based on the Rf value.

The starting material(s) is (are) prepared as follows:
a) (3R,4R,5R)-4-[4-((R)-2-Ethoxy-propoxymethyl)-phenyl]-3-[4-(3-methoxy-propyl)-3,4-dihydro-2H-benzo[1,4]oxazin-6-ylmethoxy]-5-pyrrolidin-1-ylmethyl-piperidine-1-carboxylic acid tert-butyl ester To a solution of 1 mmol of (3S,4R,5R)-4-[4-((R)-2-ethoxy-propoxymethyl)-phenyl]-3-formyl-5-[4-(3-methoxy-propyl)-3,4-dihydro-2H-benzo[1,4]oxazin-6-ylmethoxy]-piperidine-1-carboxylic acid tert-butyl ester in 5 ml of THF are added 1.2 mmol of pyrrolidine, 1.1 mmol of acetic acid and 1.5 mmol of sodium triacetoxyborohydride. The reaction mixture is stirred for 5 h, and poured on an ice $H_2O$ mixture. The mixture is extracted with TBME (3×). The combined organic phases are washed with $H_2O$ and brine, dried over sodium sulfate and concentrated under reduced pressure. The residue is purified by flash chromatography ($SiO_2$ 60F) to afford the title compound, which is identified based on the Rf value.

b) (3S,4R,5R)-4-[4-((R)-2-Ethoxy-propoxymethyl)-phenyl]-3-formyl-5-[4-(3-methoxy-propyl)-3,4-dihydro-2H-benzo[1,4]oxazin-6-ylmethoxy]-piperidine-1-carboxylic acid tert-butyl ester To a solution of 1 mmol of (3S,4R,5R)-4-[4-((R)-2-ethoxy-propoxymethyl)-phenyl]-3-hydroxymethyl-5-[4-(3-methoxy-propyl)-3,4-dihydro-2H-benzo[1,4]oxazin-6-ylmethoxy]-piperidine-1-carboxylic acid tert-butyl ester (example 1a) in 1 ml of DMSO and 5 ml of $CH_2Cl_2$ at 0° C. are added 5 mmol of $Et_3N$ and 3 mmol of pyridine sulfur trioxide complex. The reaction mixture is allowed to stir for an additional 3 h at this temperature and then allowed to warm to RT and stirred at RT for 5 h, diluted with water and acidified by the addition of 1N $KHSO_4$ and subsequently extracted with $Et_2O$. The organic phases are dried over $Na_2SO_4$ and concentrated by evaporation The residue is purified by flash chromatography ($SiO_2$ 60F) to afford the title compound, which is identified based on the Rf value.

According to the procedures described in example 12, the following compound is prepared in an analogous manner:

13 6-{(3R,4R,5S)-4-[4-((R)-2-Ethoxy-propoxymethyl)-phenyl]-5-piperidin-1-ylmethyl-piperidin-3-yloxymethyl}-4-(3-methoxy-propyl)-3,4-dihydro-2H-benzo[1,4]oxazine using piperidine instead of pyrrolidine Example 14

3-{(3S,4R,5R)-4-[4-((R)-2-Ethoxy-propoxymethyl)-phenyl]-5-[4-(3-methoxy-propyl)-3,4-dihydro-2H-benzo[1,4]oxazin-6-ylmethoxy]-piperidin-3-yl}-1-pyrrolidin-1-yl-propan-1-one According to general method A, 1 mmol of (3R,4R,5S)-4-[4-((R)-2-ethoxypropoxy-methyl)-phenyl]-3-[4-(3-methoxy-propyl)-3,4-dihydro-2H-benzo[1,4]oxazin-6-ylmethoxy]-5-(3-oxo-3-pyrrolidin-1-yl-propyl)-piperidine-1-carboxylic acid tert-butyl ester are used to provide the title compound, which is identified based on the Rf value.

The starting material(s) is (are) prepared as follows:

a) (3R,4R,5S)-4-[4-((R)-2-Ethoxy-propoxymethyl)-phenyl]-3-[4-(3-methoxy-propyl)-3,4-dihydro-2H-benzo[1,4]oxazin-6-ylmethoxy]-5-(3-oxo-3-pyrrolidin-1-yl-propyl)-piperidine-1-carboxylic acid tert-butyl ester According to general method B, 1 mmol of (3R,4R,5S)-4-[4-((R)-2-ethoxypropoxy-methyl)-phenyl]-3-[4-(3-methoxy-propyl)-3,4-dihydro-2H-benzo[1,4]oxazin-6-yl-methoxy]-5-((E)-3-oxo-3-pyrrolidin-1-yl-propenyl)-piperidine-1-carboxylic acid tert-butyl ester are used to provide the title compound, which is identified based on the Rf value.

b) (3R,4R,5S)-4-[4-((R)-2-Ethoxy-propoxymethyl)-phenyl]-3-[4-(3-methoxy-propyl)-3,4-dihydro-2H-benzo[1,4]oxazin-6-ylmethoxy]-5-((E)-3-oxo-3-pyrrolidin-1-yl-propenyl)-piperidine-1-carboxylic acid tert-butyl ester A solution of 1 mmol of (3S,4R,5R)-4-[4-((R)-2-ethoxy-propoxymethyl)-phenyl]-3-formyl-5-[4-(3-methoxy-propyl)-3,4-dihydro-2H-benzo[1,4]oxazin-6-ylmethoxy]-piperidine-1-carboxylic acid tert-butyl ester (example 12b) and 1.1 mmol of (2-oxo-2-pyrrolidin-1-yl-ethyl)-triphenyl-phosphonium chloride in 5 ml MeOH is added 1.05 mmol of $NaOCH_3$ The reaction mixture is stirred at RT overnight. The reaction mixture is quenched by addition of 0.1 N HCl and $H_2O$. The phases are separated and the organic phase is washed with saturated aqueous $NaHCO_3$ solution and brine. The combined aqueous phases are extracted with TBME. The combined organic layers are dried over $Na_2SO_4$ and concentrated by evaporation. The title compound is obtained from the residue by means of flash chromatography ($SiO_2$ 60F) and is identified based on the Rf value.

c) (2-Oxo-2-pyrrolidin-1-yl-ethyl)-triphenyl-phosphonium chloride

A solution of 1 mmol of 2-chloro-1-pyrrolidin-1-yl-ethanone [20266-00-6] in 5 ml of $CH_3CN$ is treated with 1 mmol of triphenylphosphine. The mixture is heated for 3 h to 70° C., then cooled to RT. The solvent is evaporated and the crude salt is used for the next step.

The invention claimed is:
1. A compound of the formula

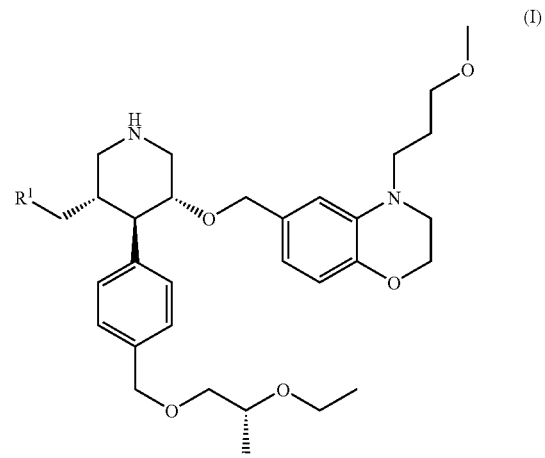

(I)

or its pharmaceutically acceptable salt, in which
$R^1$ is $C_{1-8}$-alkanoyloxy, $C_{1-8}$-alkanoyloxy-$C_{1-8}$-alkyl, $C_{1-8}$-alkoxy, $C_{1-8}$-alkoxy-$C_{1-8}$-alkoxy, $C_{1-8}$-alkoxy-$C_{1-8}$-alkoxy-$C_{1-8}$-alkyl, $C_{1-8}$-alkoxy-$C_{1-8}$-alkyl, $C_{1-8}$-alkoxycarbonylamino, $C_{1-8}$-alkoxycarbonylamino-$C_{1-8}$-alkyl, $C_{0-8}$-alkylcarbonylamino, $C_{0-8}$-alkylcarbonylamino-$C_{1-8}$-alkyl, O—$C_{1-8}$-alkylated carboxyl, O—$C_{1-8}$-alkylated carboxyl-$C_{1-8}$-alkyl, optionally N-mono- or N,N-di-$C_{1-8}$-alkylated amino, optionally N-mono- or N,N-di-$C_{1-8}$-alkylated amino-$C_{1-8}$-alkyl, optionally N-mono- or N,N-di-$C_{1-8}$-alkylated amino-carbonylamino, optionally N-mono- or N,N-di-$C_{1-8}$-alkylated amino-carbonylamino-$C_{1-8}$-alkyl, heterocyclyl, heterocyclyl-$C_{1-8}$-alkyl, heterocyclyl-$C_{0-8}$-alkyl-carbonyl-$C_{0-8}$-alkylamino, heterocyclyl-$C_{0-8}$-alkyl-carbonyl-$C_{0-8}$-alkylamino-$C_{1-8}$-alkyl, heterocyclyl-$C_{0-8}$-alkyl-carbonyl-$C_{1-8}$-alkyl, cycloalkyl-$C_{0-8}$-alkyl-carbonyl-$C_{0-8}$-alkylamino, cycloalkyl-$C_{0-8}$-alkyl-carbonyl-$C_{0-8}$-alkylamino-$C_{1-8}$-alkyl, hydroxyl, hydroxy substituted $C_{1-8}$-alkyl, optionally N-mono-, -di- or -tri-$C_{1-8}$-alkylated or heterocyclyl-substituted ureido, or optionally N-mono-, -di- or -tri-$C_{1-8}$-alkylated or heterocyclyl-substituted ureido-$C_{1-8}$-alkyl and whereby the heterocyclyl and cycloalkyl radicals mentioned hereinbefore are unsubstituted or substituted.

2. The compound according to claim 1 in which $R^1$ is hydroxyl or straight-chain omega-hydroxy substituted $C_{1-4}$-alkyl, or a pharmaceutically acceptable salt thereof.

3. The compound according to claim 1 in which $R^1$ is $C_{1-4}$-alkoxy, $C_{1-4}$-alkoxy-$C_{1-4}$-alkyl or $C_{1-4}$-alkoxy-$C_{1-4}$-alkoxy, or a pharmaceutically acceptable salt thereof.

4. The compound according to claim 1 in which $R^1$ is straight-chain $C_{1-4}$-alkoxy, straight chain $C_{1-4}$-alkoxy-straight-chain-$C_{1-4}$-alkyl or straight-chain $C_{1-4}$-alkoxy-straight-chain $C_{1-4}$-alkoxy, or a pharmaceutically acceptable salt thereof.

5. The compound according to claim 1 in which $R^1$ is $C_{0-3}$-alkylcarbonylamino or $C_{0-3}$-alkylcarbonylamino-$C_{1-4}$-alkyl, or a pharmaceutically acceptable salt thereof.

6. The compound according to claim 1 in which $R^1$ is optionally N-mono- or N,N-di-$C_{1-4}$-alkylated amino or optionally N-mono- or N,N-di-$C_{1-4}$-alkylated amino-$C_{1-4}$-alkyl, or a pharmaceutically acceptable salt thereof.

7. The compound according to claim 1 in which $R^1$ is optionally substituted, N-bound saturated N-containing $C_{5-6}$-heterocyclyl, or a pharmaceutically acceptable salt thereof.

8. The compound according to claim 1 in which $R^1$ is hydroxy, hydroxy-$C_{1-2}$-alkyl, $C_{1-2}$-alkoxy, 2-methoxy-ethoxy, acetyloxy, $C_{0-2}$-alkylcarbonylamino, $C_{0-2}$ monoalkylamino, N-bound pyrrolidinyl, N-bound piperidinyl or N-bound pyrrolidinyl-carbonyl-$C_{1-2}$-alkyl, or a pharmaceutically acceptable salt thereof.

9. The compound:
(3S,4R,5R)-4-[4-((R)-2-Ethoxy-propoxymethyl)-phenyl]-3-hydroxymethyl-5-[4-(3-methoxy-propyl)-3,4-dihydro-2H-benzo[1,4]oxazin-6-ylmethoxy]-piperidine-1-carboxylic acid tert-butyl ester, or a pharmaceutically acceptable salt thereof.

10. A method of treatment of high blood pressure, glaucoma, myocardial infarction, or diabetic nephropathy, comprising administering to a subject a therapeutically effective amount of a compound according to claim 1 or a pharmaceutically acceptable salt thereof.

11. A pharmaceutical composition comprising a compound according to claim 1 and one or more agents having cardiovascular activity.

12. The pharmaceutical composition according to claim 11 in which the agents having cardiovascular activity are selected from the group consisting of alpha- and beta-blockers, vasodilators, calcium antagonists, ACE inhibitors, potassium activators, antiserotoninergics, thromboxane synthetase inhibitors, neutral endopeptidase inhibitors (NEP inhibitors), angiotensin II antagonists, diuretics and sympatholytics.

* * * * *